US00PP20751P2

(12) United States Plant Patent
Trucks

(10) Patent No.: US PP20,751 P2
(45) Date of Patent: Feb. 16, 2010

(54) ***PENNISETUM* PLANT NAMED 'DESERT PLAINS'**

(50) Latin Name: *Pennisetum alopecuroides*
Varietal Denomination: Desert Plains

(76) Inventor: Gary M. Trucks, 1460 Hillandale Rd., Benton Harbor, MI (US) 49022

( * ) Notice: Subject to any disclaimer, the term of this patent is extended or adjusted under 35 U.S.C. 154(b) by 0 days.

(21) Appl. No.: 12/220,198

(22) Filed: Jul. 22, 2008

(51) Int. Cl.
*A01H 5/00* (2006.01)

(52) U.S. Cl. ..... Plt./384

(58) Field of Classification Search ..... Plt./384
See application file for complete search history.

*Primary Examiner*—Susan B McCormick Ewoldt

(57) ABSTRACT

A new and distinct cultivar of ornamental Fountain Grass, *Pennisetum alopecuroides* 'Desert Plains', with vase-shaped habit, broad foliage that develops early colors of red and orange, begins flowering in August and lasting through the winter.

3 Drawing Sheets

Botanical classification: *Pennisetum alopecuroides*.
Variety denomination: 'Desert Plains'.

SUMMARY, BACKGROUND AND ORIGIN OF THE PLANT

*Pennisetum alopecuroides* 'Desert Plains', hereinafter also referred to as 'Desert Plains' and "the plant" is a new and distinct cultivar of Fountain Grass. It is an open pollinated seedling of *Pennisetum alopecuroides* 'Cassian' (not patented) by Gary M. Trucks. The seed was collected in the fall of 2001 and grown out in the spring of 2002. It was selected for further evaluation that summer of 2002. The nearest comparisons to *Pennisetum* 'Desert Plains' would be 'Cassian' (not patented) and 'Hameln'(not patented). The plant has been successfully asexually propagated by division at the same perennial plant nursery in Benton Harbor, MI and found to produce identical plants that maintain the unique characteristics of the original plant. The plant is stable and reproduces true to type in successive generations of asexual reproduction.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
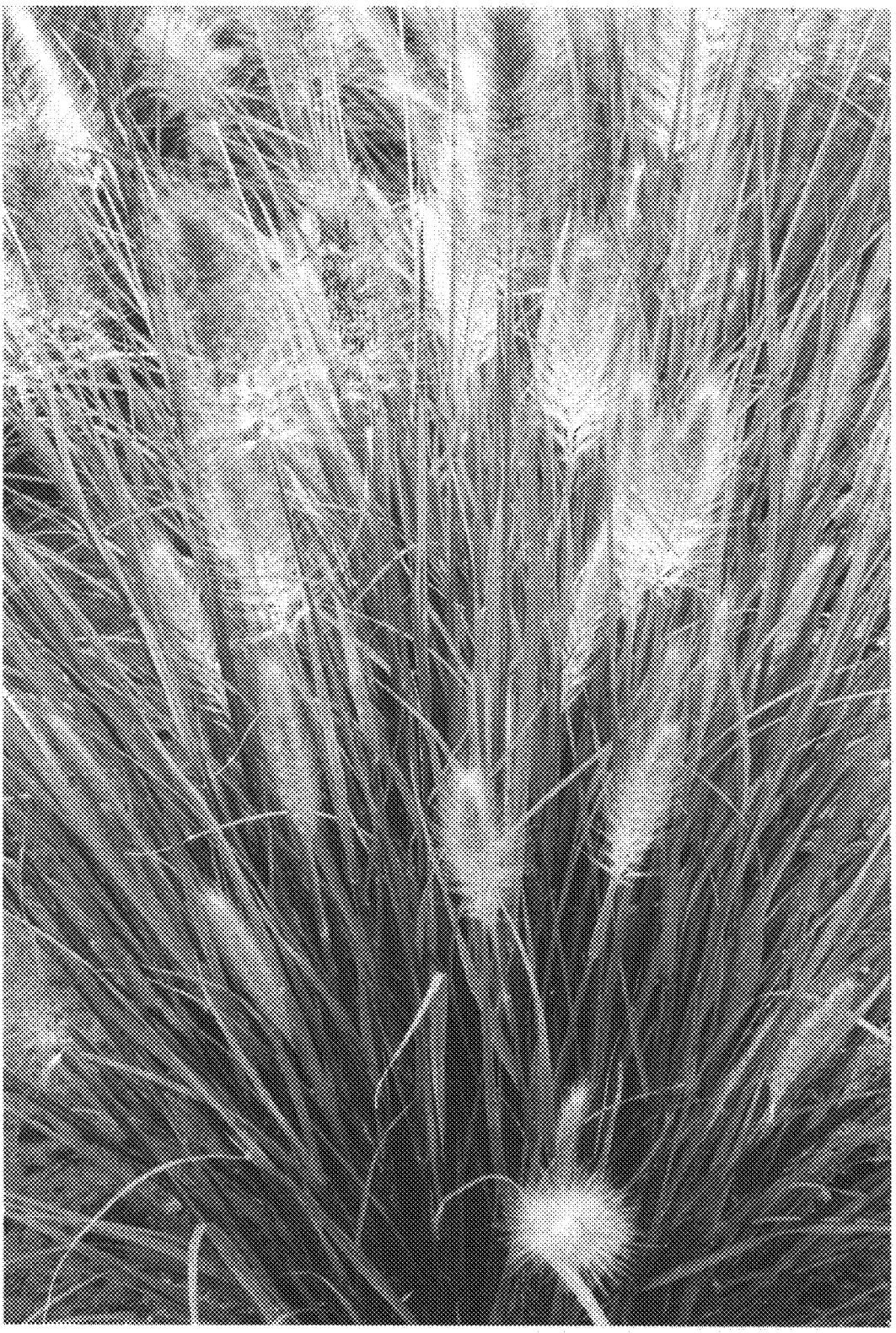
FIG. 1 shows the overall plant in early flowering.
Figure 2:
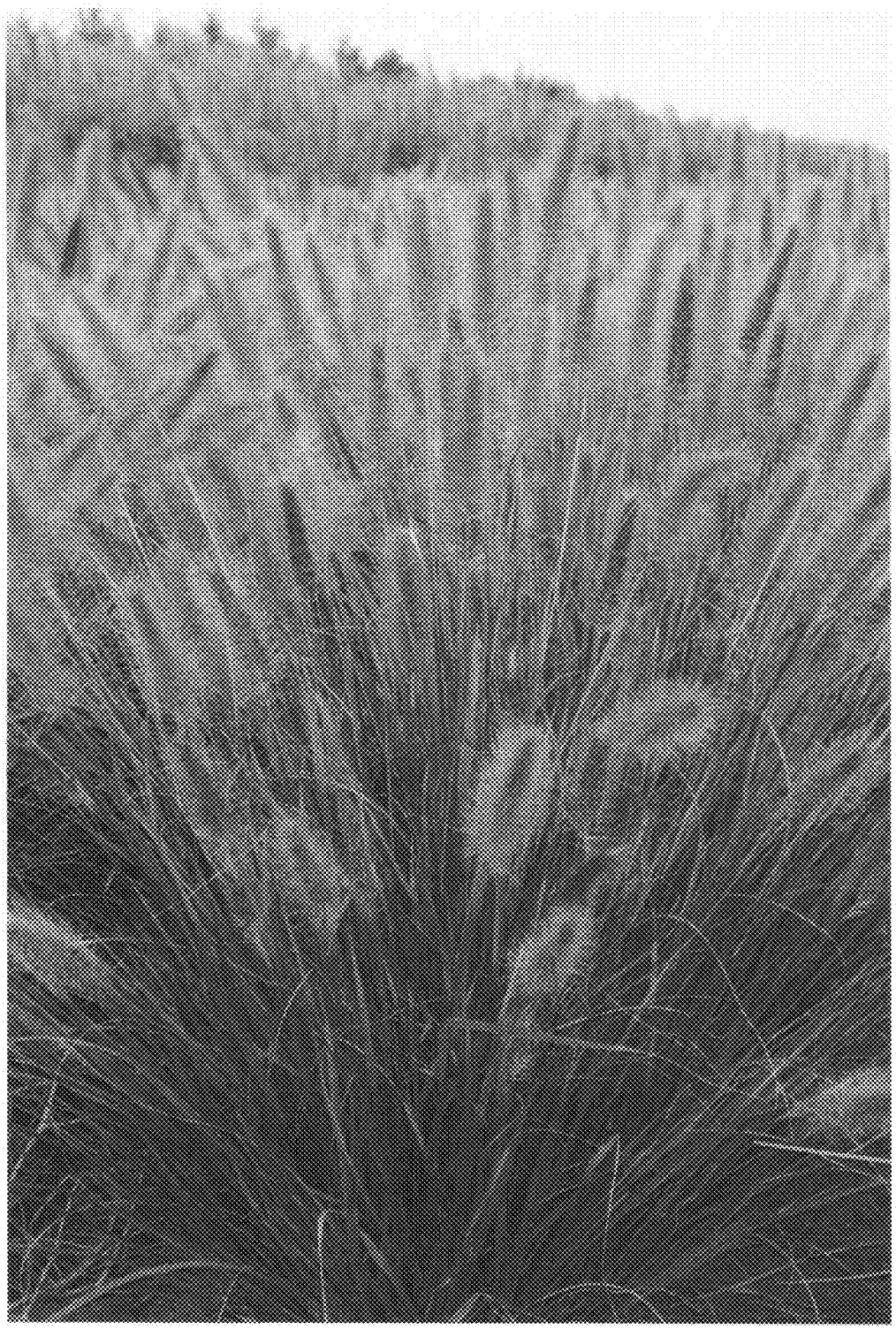
FIG. 2 shows overall plant in later season.
Figure 3:
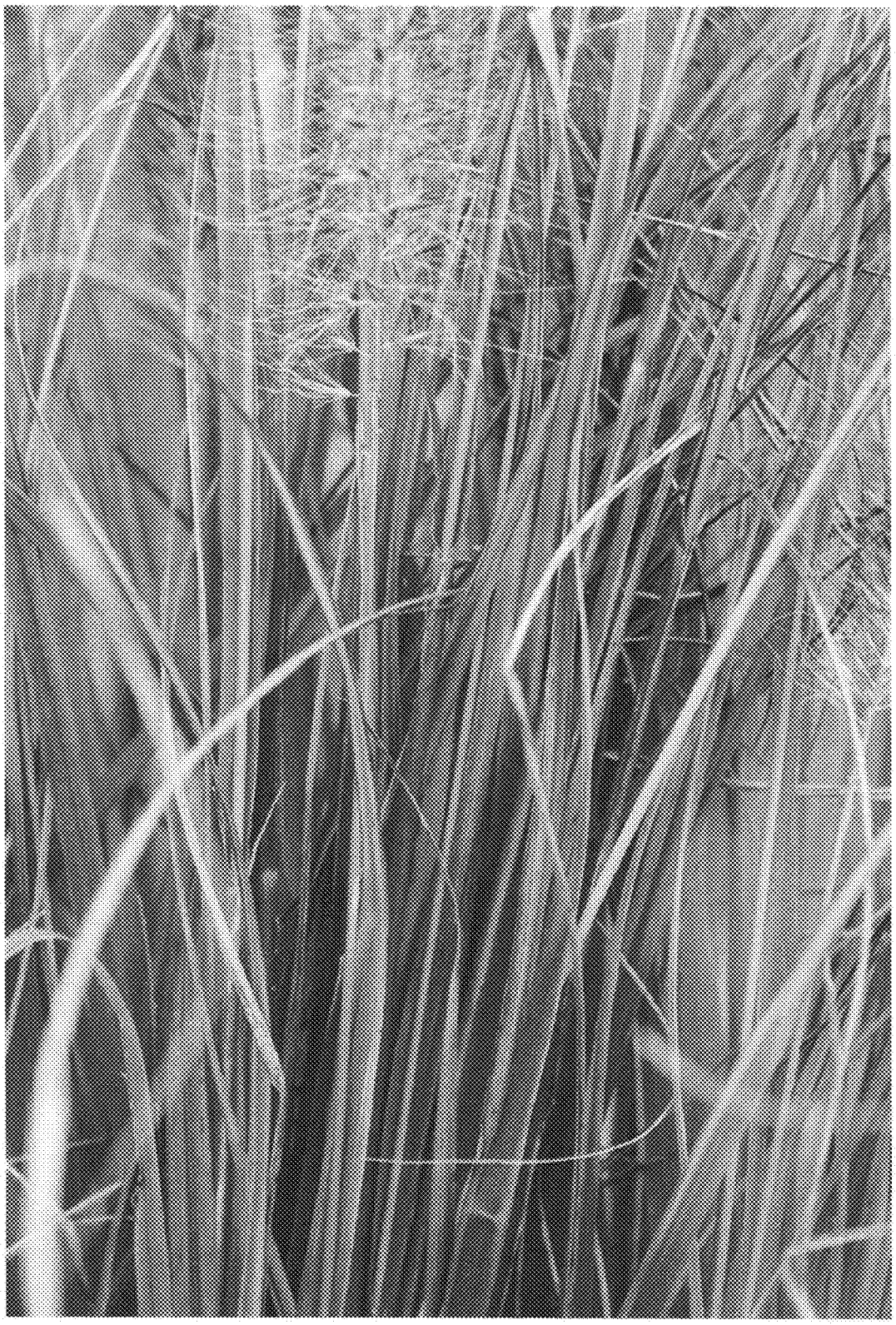
FIG. 3 shows a close up of the fall foliage color.

The new plant is nearly twice the height of 'Hameln' and is more upright and vase-shaped than 'Cassian'. 'Desert Plains' differs from its parent as well as all other *Pennisetum* known to the applicant by the following unique traits:

1. The plant develops into a taller more vase-shaped habit.
2. It has broader foliage.
3. Foliage develops early colors of red and orange foliage that begin in August.

4. Bloom period starts in September with the plumes persisting into late fall and early winter.

DETAILED BOTANICAL DESCRIPTION

The following descriptions and color references are based on the 2001 edition of The Royal Horticultural Society Colour Chart except where common dictionary terms are used. The new plant, 'Desert Plains', has not been observed under all possible environments. The phenotype may vary slightly with different environmental conditions, such as temperature, light, fertility, moisture and maturity levels, but without any change in the genotype. The following observations and size descriptions are of a three-year old plant in a trail garden in Benton Harbor, Mich. in full sun with supplemental water and fertilizer.

Parentage: Open pollinated selection of *Pennisetum* 'Cassian'.

*Propagation method.*—By division of the rhizomes in early spring or tissue culture.

*Time to finishing in a* 65 *cm pot.*—Three months.

*Rooting habit.*—Normal, coarsely branching.

Plant description:

*Plant shape and habit.*—Hardy herbaceous perennial grass forming tightly rhizomatous clump, with upright vase-shaped culms topped with finely textured airy inflorescence.

*Plant size.*—Foliage height at flowering is 80 to 96 cm tall from soil line to the top of the leaves and 22 to 30 cm wide at soil line and 65 to 85 cm at widest point at flowers;

Foliage description: glabrous, entire, flat, alternate, erect to arching toward tips, sheathed from node of attachment to ligule, linear, leaves about 2.5 cm to 7.5 cm apart, deciduous but persist through winter;

*Foliage size.*—30 to 38 cm long, averaging 36 cm; 3 to 5 mm wide, averaging 4 mm;

Adaxial side early season: closest to RHS 133B.

Abaxial side early season: between RHS 136B and RHS 136C; Leaf tips developing tips of RHS 59A on both surfaces.

Adaxial side early fall season and later: edges of RHS N1144B with other colors nearest RHS 22A, closest to RHS 163B, more red than RHS 45A and more orange than RHS 45B Adaxial side early fall season and later: colors identical to adaxial side; Veins: parallel; colors variable, but identical to surrounding leaf on both the top and bottom of the leaf;

*Culm.*—Erect, cylindrical, completely enclosed by leaf sheath, 2 to 4 mm wide, 80 to 100 cm long including panicle, internode length 2.5 to 7.5 cm;

*Flower description.*—Finely branched open panicle, about 200 to 300 flowers per panicle, usually one panicle per culm, persists through winter; No fragrance detected;

Panicle: pubescent, numerous flowers spread on the terminal 7 to 8 cm of the rachis; about 2.5 cm wide;

Glumes: lowest outside—about 3 mm long and 1 mm wide RHS 143B; inside about 4 mm long and 1 mm wide, RHS 143B;

Bristles: 1 to 1.5 cm long and less than 1 mm wide, closest to RHS N186D at base and RHS 192D at apex;

*Gynoecium.*—Stigma: two, feathered, protruding 1 to 2 mm from glume, RHS 59A.

*Androecium.*—Filaments: fine, hair-like, white, lighter than RHS 11A, less than 1 mm diameter and up to 2.0 mm long;

Anthers: 2.0 to 3.0 mm long, 1.0 mm wide, closest to RHS 31A.

*Pollen.*—Elliptical, less than 0.1 mm long, nearest RHS N 25C.

*Fruit.*—Caryopsis; oblong with pointed apex and base, 2 to 3 mm long and 1.5 mm wide, nearest RHS 164C.

Hardiness, pest and disease resistance: The plant grows best with plenty of moisture and adequate drainage, but is able to tolerate some drought when mature. Hardiness at least from USDA zone 4 through 9. Disease and pest resistance beyond what is typical of that of other Fountain Grass has not been observed.

I Claim:

1. A new and distinct cultivar of ornamental *Pennisetum* plant named 'Desert Plains' as herein described and illustrated, with vase-shaped habit, broad foliage that develops early colors of red and orange foliage, begins flowering in August, holds through winter and is suitable as a potted plant, for the garden, and for cut flower arrangements.

* * * * *

Pennisetum plant named 'Desert Plains'

Pennisetum plant named 'Desert Plains'

Pennisetum plant named 'Desert Plains'